(12) United States Patent
Topf

(10) Patent No.: US 7,360,345 B2
(45) Date of Patent: Apr. 22, 2008

(54) BEVERAGE BOTTLE CAP TREATMENT DEVICE

(75) Inventor: Roland Topf, Hamburg (DE)

(73) Assignee: KHS Maschinen- und Anlagenbau AG, Dortmund (DE)

( * ) Notice: Subject to any disclaimer, the term of this patent is extended or adjusted under 35 U.S.C. 154(b) by 369 days.

(21) Appl. No.: 11/061,773

(22) Filed: Feb. 18, 2005

(65) Prior Publication Data

US 2005/0247028 A1    Nov. 10, 2005

Related U.S. Application Data

(63) Continuation-in-part of application No. PCT/EP03/08862, filed on Aug. 9, 2003.

(30) Foreign Application Priority Data

Aug. 19, 2002  (DE) .................................. 102 38 633

(51) Int. Cl.
  *B65B 55/10*  (2006.01)
  *B67B 1/03*  (2006.01)
(52) U.S. Cl. ............................. 53/426; 53/471; 53/290
(58) Field of Classification Search ................. 53/426, 53/471, 141, 167, 281, 290
See application file for complete search history.

(56) References Cited

U.S. PATENT DOCUMENTS

| 2,278,434 | A |   | 4/1942  | Fahey |            |
|-----------|---|---|---------|----------------|--------|
| 3,318,439 | A |   | 5/1967  | Sullivan |          |
| 5,848,515 | A | * | 12/1998 | Catelli et al. | 53/167 |
| 5,857,309 | A | * | 1/1999  | Cicha et al.   | 53/167 |
| 6,256,964 | B1| * | 7/2001  | Drevfors       | 53/426 |
| 6,341,472 | B1| * | 1/2002  | Schroeder      | 53/426 |
| 6,484,477 | B1| * | 11/2002 | Bernhard       | 53/426 |
| 2007/0006550 | A1 | * | 1/2007 | Kemper et al. | 53/426 |
| 2007/0157552 | A1 | * | 7/2007 | Cirio         | 53/306 |

FOREIGN PATENT DOCUMENTS

| JP | 11342917   | 12/1999 |
|----|------------|---------|
| WO | WO 98/46486 | 10/1998 |
| WO | WO 00/46142 | 10/2000 |

* cited by examiner

*Primary Examiner*—Hemant M. Desai
(74) *Attorney, Agent, or Firm*—Nils H. Ljungman & Associates

(57) ABSTRACT

A treatment device handles and treats bottle or container caps, which treatment device may be used in a capping machine in a beverage bottle or container filling plant. The treatment device transports the caps on carrier rings and transfer chutes inside a housing, which has a flow of treatment gas traveling therethrough to treat the caps.

20 Claims, 5 Drawing Sheets

BEVERAGE BOTTLE CAP TREATMENT DEVICE

CONTINUING APPLICATION DATA

This application is a Continuation-In-Part application of International Patent Application No. PCT/EP2003/008862, filed on Aug. 9, 2003, which claims priority from Federal Republic of Germany Patent Application No. 102 38 633.1, filed on Aug. 19, 2002. International Patent Application No. PCT/EP2003/008862 was pending as of the filing date of this application. The United States was an elected state in International Patent Application No. PCT/EP2003/008862.

BACKGROUND

1. Technical Field

The present application relates to a beverage bottling plant for filling bottles with a liquid beverage material having a treatment device for the treatment of bottle caps.

2. Background Information

A beverage bottling plant for filling bottles with a liquid beverage filling material can possibly comprise a beverage filling machine with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine. Upon filling, a closing station closes the filled bottles. There may further be provided a conveyer arrangement configured to transfer filled bottles from the filling machine to the closing station. Bottles may be labeled in a labeling station, the labeling station having a conveyer arrangement to receive bottles and to output bottles. The closing station and the labeling station may be connected by a corresponding conveyer arrangement.

When the quality requirements for the beverage being bottled are stringent, caps on beverage containers, such as screw-on caps, crown corks, can covers etc. must be treated prior to installation on the beverage container. To meet these requirements, the conventional treatment methods expose the caps to a gas atmosphere that either has a sterilizing effect itself or dries treatment liquids such as e.g. $H_2O_2$ that have been applied to the surfaces of the caps. For this purpose, the caps must be exposed to a defined atmosphere for a relatively long time.

Since in modern container handling machines, the caps are guided in tracks, generally a single track, to make an orderly sequence of operations possible, they must also be guided in tracks in the treatment device. If we take into consideration the current processing speeds of cap closing machines, and given the length of time the caps must be held in the treatment device, the result is a distance of several meters. When the track is realized in the form of a chute or a driven conveyor, that can cause significant problems in terms of space and construction.

A similar treatment device of the prior art is known from WO 00/46142 A2. In a closed housing through which the handling atmosphere circulates, the track is arranged so that it makes a plurality of revolutions around a vertical axis. This arrangement has the advantage that it makes it possible to install a long track in a small three-dimensional space, thereby solving space problems.

One disadvantage of this construction is the helical, stationary realization of the trajectory on which the caps move by sliding over the entire length of the trajectory. In view of the relatively flat inclination of the helix which is necessary to reduce the amount of space the system takes up, the caps do not slide exclusively as a result of the angle of inclination of the track, but require additional propulsion—several different realizations of which are explained in the above-referenced prior art document—either by means of air blown in through nozzles or with a rotating drum that drives the caps engaged in slots. The result is an extraordinarily complicated construction which is also susceptible to jams and backups.

OBJECT OR OBJECTS

The object is to create a treatment device of the type described above that has a simpler construction and is also less susceptible to malfunctions and jamming.

The present application teaches that this object can be accomplished with the features disclosed herein below.

SUMMARY

The present application teaches that the caps run one after another on a plurality of encircling horizontal carrier rings that are arranged one above the other, are self-propelled and thus transport the caps in a horizontal position over a large rotational angle. In one sector of the device, transfer chutes are located above one another, each of which accepts the caps from a carrier ring and transfers them to the next-lower carrier ring by allowing them to slide downward a short distance. The construction of this device is very simple. It requires essentially a plurality of driven carrier rings that move in synchronization above one another, as well as the stationary transfer chutes. The danger of malfunctions and jams is significantly less than in the construction of the prior art, because with when the caps are transported in the horizontal position on the carrier rings, there is less danger of a malfunction and the risk of problems is very low in the relatively short transfer chutes. The carrier rings can be located one above another essentially at the interval of the cap heights, so that a very long trajectory can be covered in a relatively small housing.

The carrier rings need only be capable of carrying the caps securely so that they cannot fall through. The lateral guides that form the boundaries of the trajectory on the carrier rings can be realized in the form of simple metal sheets. The features disclosed herein below are advantageous for this purpose, whereby the carrier rings and/or the lateral guides are realized so that they are gas-permeable. Therefore, during the transport of the caps, it is guaranteed that the caps will be exposed to a strong flow with a good circulation of the atmosphere that flows through the surrounding housing. The carrier rings can thereby be realized in the form of ring-shaped parallel rods, for example. The metal sheets installed to serve as lateral borders can be perforated or can also be realized in the form of grids or meshes.

The caps can be fed to the topmost carrier ring and removed from the bottom-most carrier ring by all means suitable for these purposes, such as with transfer star wheels, for example. However, other advantageous features that result in a particularly simple construction with a good feed and removal of the caps from the respective carrier rings could be that the feed could be realized so that its terminal piece matches the terminal piece of a transfer chute, and/or that the discharge could be realized so that its beginning piece matches the beginning piece of a transfer chute.

An additional advantageous feature could be that the carrier rings are driven in synchronization with one another. The construction thereby becomes significantly simpler compared to special constructions that are also possible in the context of this embodiment with individual drives for the carrier rings, which can be realized in the form of individually driven wheels, for example.

Advantageous features are also disclosed, according to which the carrier rings are fastened one above another to the external cylindrical surface of a revolving drum, which makes possible a very simple construction. The drum can thereby form the internal lateral guide that travels along with the carrier rings and thus further reduces the danger of jamming. The drum offers the additional advantage that it can be realized in the form of a closed drum and can thus form the inner boundary of the space inside the closed housing filled with the treatment atmosphere.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The embodiments are explained in greater detail below and are illustrated schematically in the accompanying drawings, in which.

DESCRIPTION OF EMBODIMENT OR EMBODIMENTS

Figure 1:
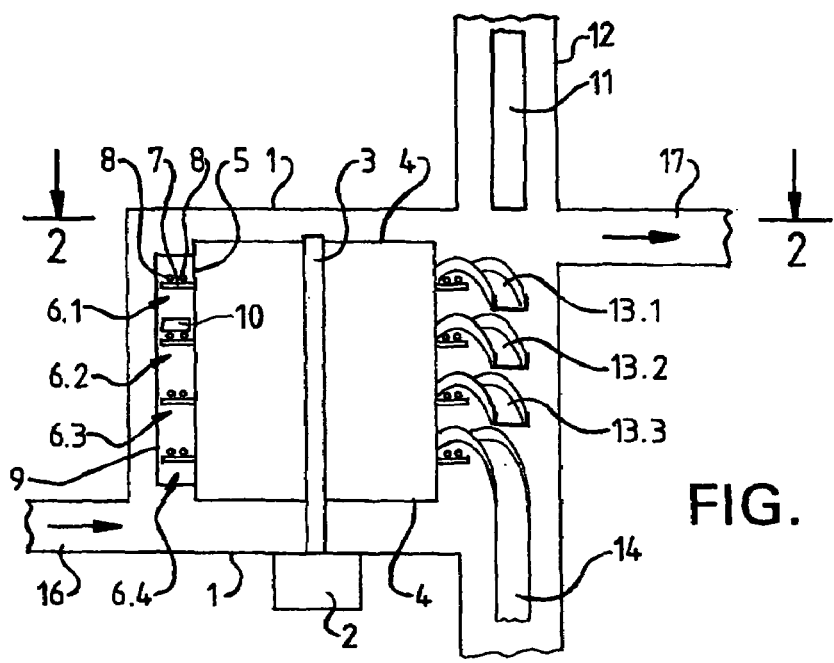
FIG. 1 is an axial section through a sterilizing device as taught by one possible embodiment along Line 1-1 in FIGS. 2 and 3.
Figure 1A:
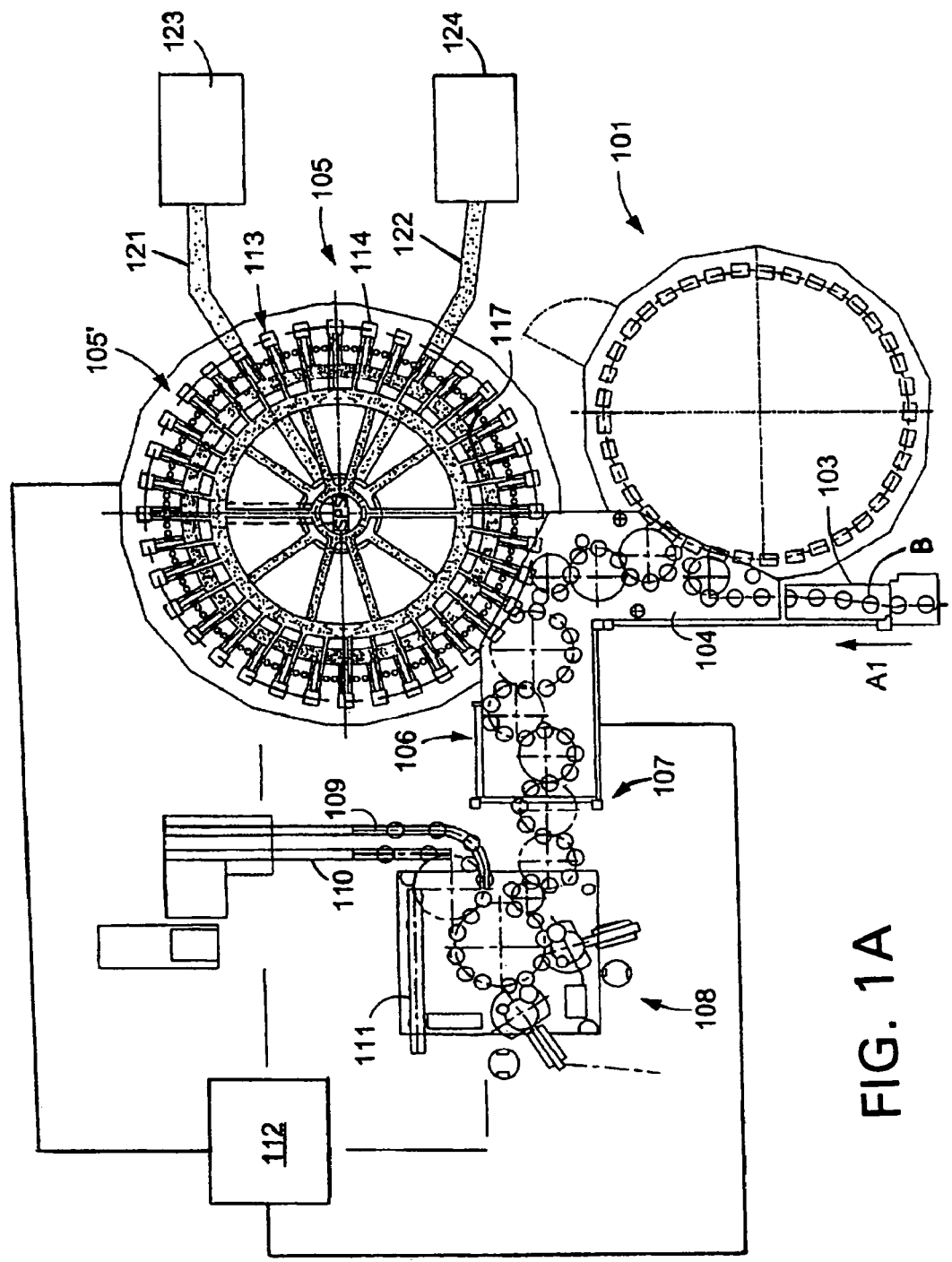
FIG. 1A is a schematic illustration of a container filling plant in accordance with one possible embodiment.

FIG. 1A shows schematically the main components of one possible embodiment example of a system for filling containers, specifically, a beverage bottling plant for filling bottles B with at least one liquid beverage, in accordance with at least one possible embodiment, in which system or plant could possibly be utilized at least one aspect, or several aspects, of the embodiments disclosed herein.

FIG. 1A shows a rinsing arrangement or rinsing station 101, to which the containers, namely bottles B, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles B are transported to a beverage filling machine 105 by a second conveyer arrangement 104 that is formed, for example, by one or more starwheels that introduce bottles B into the beverage filling machine 105.

The beverage filling machine 105 shown is of a revolving or rotary design, with a rotor 105', which revolves around a central, vertical machine axis. The rotor 105' is designed to receive and hold the bottles B for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles B to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1A, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle B, the first product or the second product can be filled by means of an appropriate control of the filling product or fluid valves.

Downstream of the beverage filling machine 105, in the direction of travel of the bottles B, there can be a beverage bottle closing arrangement or closing station 106 which closes or caps the bottles B. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles B. In the embodiment shown, the labeling arrangement 108 has three output conveyer arrangement: a first output conveyer arrangement 109, a second output conveyer arrangement 110, and a third output conveyer arrangement 111, all of which convey filled, closed, and labeled bottles B to different locations.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

As shown in the figures, which show different views of the same exemplary embodiment, in a housing 1 there is a vertical shaft 3 that is driven by a motor 2. This shaft drives a drum comprising end walls 4 and a cylindrical peripheral wall 5. The drum 4, 5 rotates in the direction indicated by the arrow in FIG. 2.

Fastened to the periphery of the drum 4, 5 are four carrier rings 6.1-6.4. In the illustrated exemplary embodiment, these carrier rings comprise a plurality of pins 7 that are fastened to the peripheral wall 5 of the drum so that the extend radially, with two ring-shaped rods 8 that are fastened to said pins and run concentrically around the peripheral wall 5 of the drum.

In another possible embodiment, the carrier rings could possibly be connected directly to the vertical shaft 3, such as by rods or arms for example. In this possible embodiment, the vertical shaft 3 may not comprise a drum.

Figure 2:
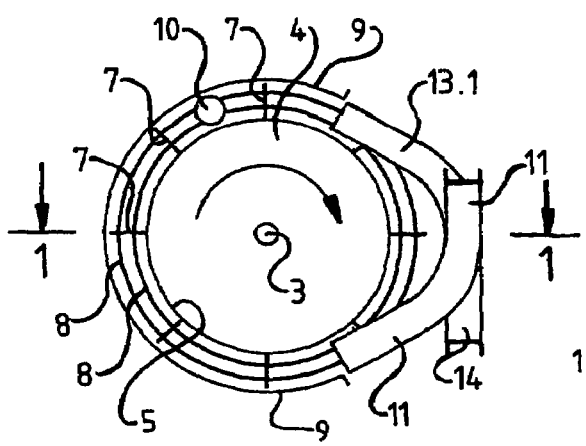
FIG. 2 is an axial section of the internal parts of the sterilizing device, shown without the housing, in a sectional view along Line 2-2 in FIG. 1.

Over more than one-half of the periphery, running around the carrier rings 6.1-6.4, is an outer guide plate 9 which is stationary. FIGS. 1 and 2 each show a cap 10 lying on the ring-shaped rods 8 of a carrier ring 6. The figures show that the caps 10 are lying securely on the ring-shaped rods 8 and are guided on the concentric track thereby formed by the guide plate 9 as an outer lateral guide and the peripheral wall 5 as an inner lateral guide. The caps 10 are transported by the rotational movement of the carrier rings 6 with the drum 4, 5.

Figure 3:
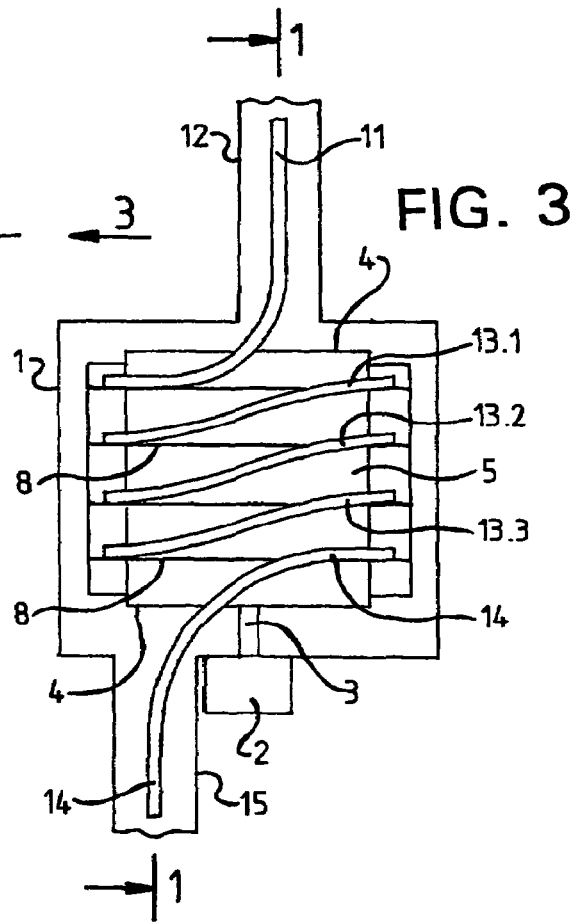
FIG. 3 is a side view along Arrow 3 in FIG. 2, shown with the housing.

A feed 11 in the form of a chute with the conventional rectangular guide profile, as shown in FIGS. 1 and 3, leads from the top through a conduit 12 that is provided with an entry loop (not shown) into the interior of the housing 1 where, as shown in FIGS. 2 and 3, it runs along a curve to the topmost carrier ring 6.1, where it feeds the caps 10 onto the topmost carrier ring 6.1 where they slide down one after the other by gravity.

In another possible embodiment, a feed 11 could empty into the housing 1 from above, and through said feed 11 a feed chute could run downward and in a curve and end with its end flat on the topmost carrier ring 6.1. The feed chute could be configured in an angular U-shape with lateral boundary walls or could be realized in the form of a closed profile to prevent the loss of the caps even when they are being guided vertically.

After the end of the feed 11, the caps are lying on the topmost carrier ring 6.1 and travel with it until they reach the beginning of a first transfer chute 13.1, which is also realized with the rectangular profile which is conventionally used for such chutes. The transfer chute 13.1 runs from its beginning in the manner visible in FIGS. 1, 2 and 3 and is pivoted outward and downward from a receiving position on the uppermost carrier ring 6.1 to a discharge position on the next-lower carrier ring 6.2, which trails it by one angular sector.

Below the topmost transfer chute 13.1 are two additional and identical transfer chutes 13.2 and 13.3, each of which receives caps from the next-higher carrier ring and delivers them to the next-lower carrier ring. In this manner, the caps travel from the topmost carrier ring 6.1 to the next lower carrier ring 6.2, then to 6.3 and finally to 6.4, from where they are removed from the lowest carrier ring 6.4 by means of a discharge, the initial sector of which is realized in a manner similar to a transfer chute, and are discharged out of the housing 1 downward through a conduit 15.

In one possible embodiment, the transfer chutes may be coated with a low-friction coating to promote easier transport of bottle caps and to discourage blockages.

Figure 1B:
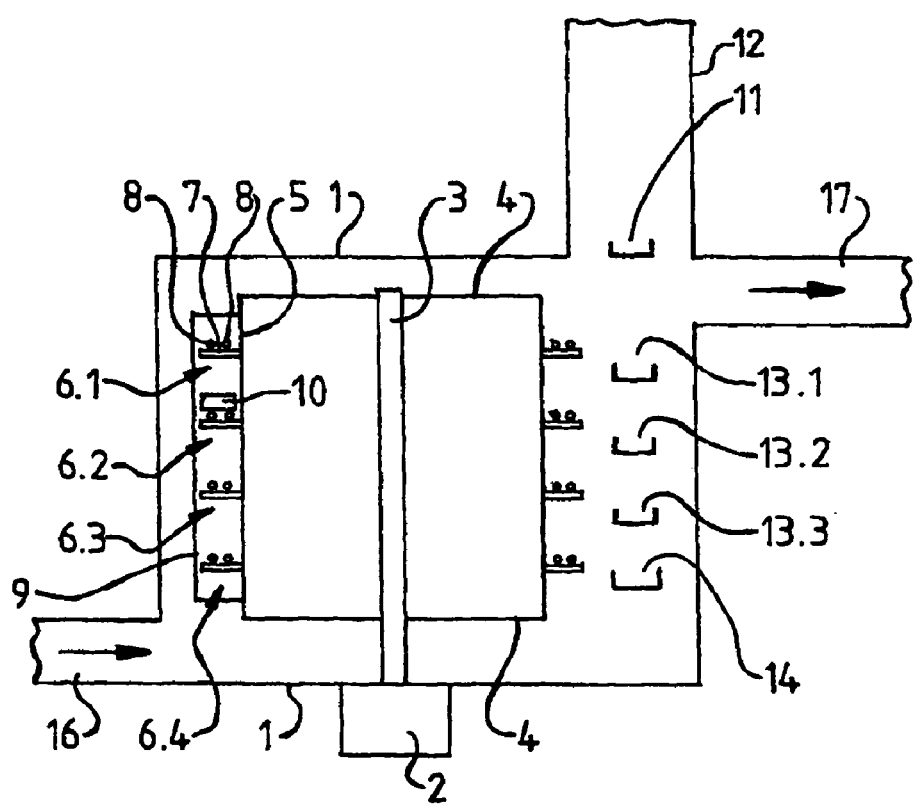
FIG. 1B is similar to FIG. 1, and shows a cross-sectional view of another possible embodiment of a sterilizing device.
Figure 3A:
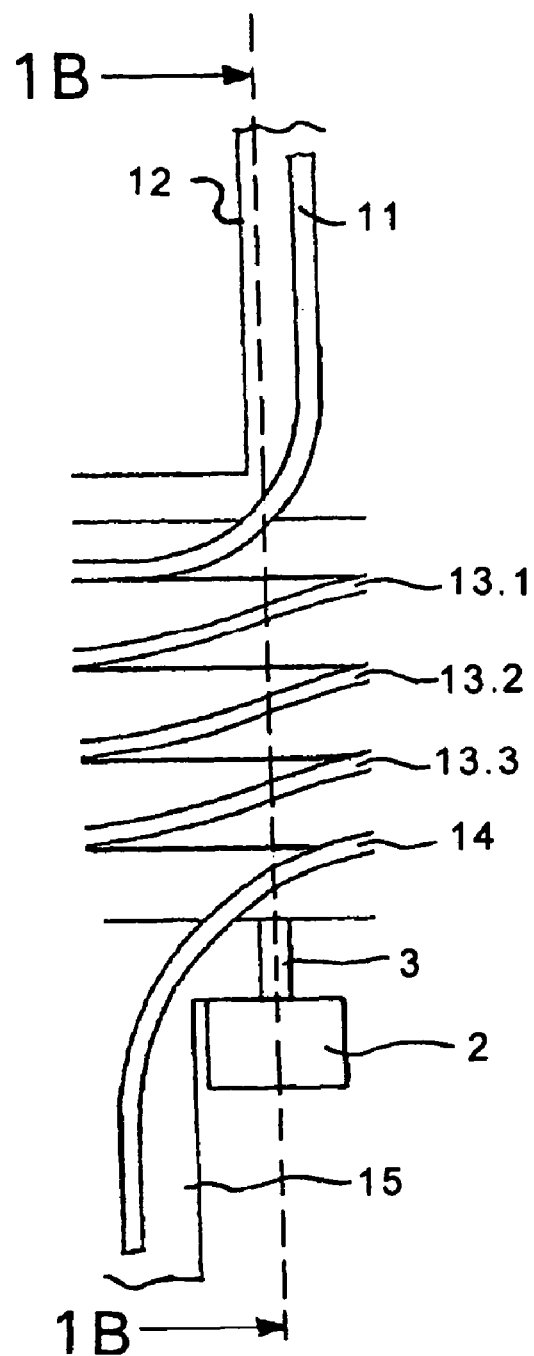
FIG. 3A is a blown-up view of a section of the embodiment shown in FIG. 3.

FIG. 1B shows a cross-sectional view along the line 1B-1B in FIG. 3A. From this view, only cross-sections of the feed 11, the transfer chutes 13.1, 13.2, and 13.3, and the discharge chute 14 that lie in the plane defined by line 1B-1B can be seen.

As shown in FIG. 2 in particular, the transfer chutes 13.1 to 13.3 lie in the sector of the drum 4, 5 that is not encircled by the guide sheet 9.

FIG. 1 shows that the interior of the housing 1 is supplied with gas via an inflow conduit 16, so that the gas flows out of the housing through an exhaust conduit 17. The gas route, as shown in FIG. 1, runs essentially in countercurrent to the travel of the caps 10 through the housing 1. The gas flowing through can be a sterilizing gas, for example. However, before they enter the housing 1, the caps 10 can be sprayed with a sterilizing liquid, for example, which is then dried off in the interior of the housing 1, e.g. using a flow of hot air.

Guide devices (not shown) for the gas flow can be provided in the interior of the housing 1 to steer the gas flow to defined advantageous paths, for example essentially in the annular space between the peripheral wall 5, the drum 4, 5 and the surrounding guide plate 9 so that it flows upward through the carrier rings 6.4-6.1. The guide plate 9 can also be perforated or in the form of a grid, for example, to make possible an unrestricted flow of gas.

In the embodiment illustrated in the figures, the caps 10 are guided in a single track on the illustrated chutes 11, 14, 13.1-13.3 and on the carrier rings 6.1-6.4. When these elements are made wider, the caps can also be guided in several tracks.

In the illustrated embodiment, the chutes 11, 13.1-13.3 and 14 are realized in the form of rectangular sheet metal profiles. However, these chutes can also be realized in the conventional manner as guide rods with supporting rods and lateral boundary rods. The flow of gas around the caps 10 is also thereby improved in this area. In this case, on the transfer chutes 13.1-13.3, the lateral boundaries can be realized in the form of metal sheets that are continuous from top to bottom, and are provided in this area in a manner similar to the guide plate 9.

Figure 2A:
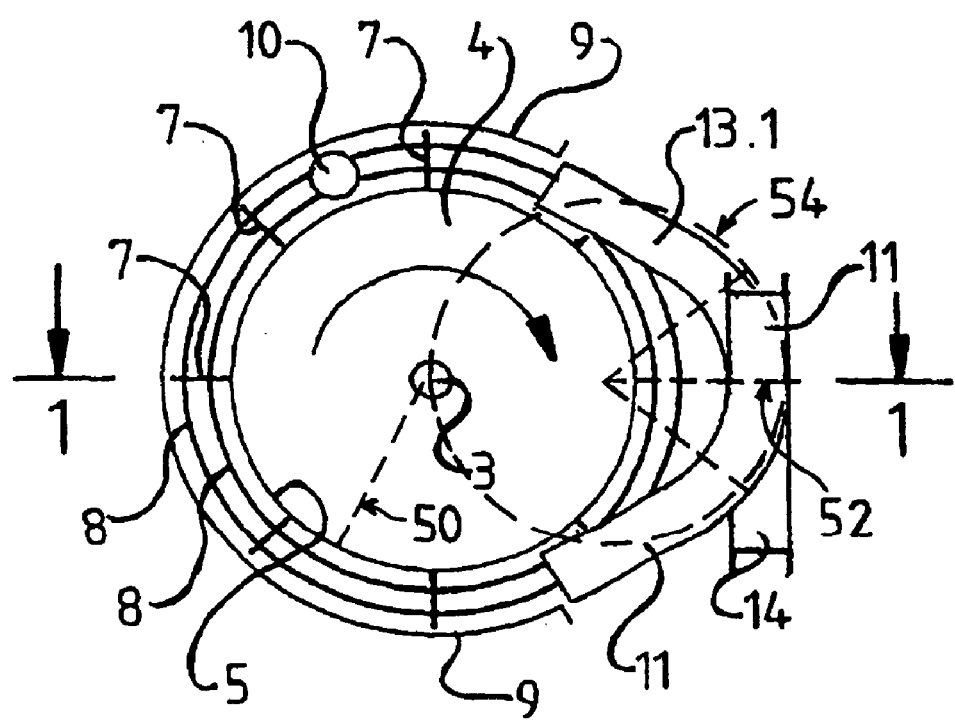
FIG. 2A is similar to FIG. 2, and shows possible dimensions of one possible embodiment.

FIG. 2A is similar to FIG. 2, and shows an overhead view of one possible embodiment and possible dimensions therefor. In order for the transfer chutes 13.1-13.3 to effectively guide bottle caps from one carrier ring to the carrier ring below it, the transfer chutes must project away from, and then back towards, the carrier rings at a certain curvature and at a certain angle. Therefore, the transfer chutes 13.1-13.3 are each designed to lay flat on a carrier ring in order to receive bottle caps. The flat portion then extends outwardly and downwardly away from the carrier ring. The transfer chutes 13.1-13.3 then slope downwardly toward the next-lower carrier ring, permitting the bottle caps to be forced by gravity down the slope of the transfer chute. The sloped portion then extends downwardly and inwardly toward the next-lower carrier ring, ending with the transfer chute's end lying flat on the carrier ring. At this point, bottle caps slide onto the carrier ring to be rotated toward the next transfer chute.

FIG. 2A further shows the ratio of the curvatures of the cylindrical drum and the transfer chutes according to one possible embodiment. In order to effectively transfer bottle caps from an upper carrier ring to a lower carrier ring without jamming or backing up of the bottle caps, but while still maintaining a compact design of the treatment device, the curvatures of the transfer rings 13.1-13.3 to the cylindrical drum could have a certain ratio. For example, an imaginary circle 54 could be defined by the curvature of the transfer chutes 13.1-13.3. In one possible embodiment, the ratio of the radius 50 of the cylindrical drum to the radius 52 of the imaginary circle 54 could possibly be approximately between 0.81, 0.82, 0.83, 0.84, 0.85, 0.86, 0.87, 0.88, 0.89, 0.90, and 0.91. Please note that the above range of ratios is only included herein as an example of a possible embodiment for exemplary purposes, and is not meant to limit the design of the transfer chutes in any way.

FIG. 3A shows a blown-up section of the embodiment shown in FIG. 3 and is included for clarification purposes. Line 1B-1B is the axis of the vertical shaft 3, about which the cylindrical drum rotates. A cross-sectional view along line 1B-1B of the treatment device shown in FIG. 3A is shown in FIG. 1B.

In one possible embodiment, the treatment device may be configured such that bottle caps may be transported through the treatment device for a desired length of time in order to thoroughly sterilize the bottle caps.

In another possible embodiment, the carrier rings could each be connected to individual drive systems to individually drive each of the carrier rings independent of one another.

In one possible embodiment, the present application teaches a sterilizing device for caps (10) for beverage containers, whereby the caps are guided along a trajectory in at least one track, with a closed housing (1) through which gas flows and through which the trajectory (11, 6.1-6.4, 13.1-13.3, 14) runs, whereby the trajectory is arranged inside the housing (1) so that it runs downward while encircling a vertical axis (3) a plurality of times, characterized by the fact that for each revolution, a carrier ring (6.1-6.4) that is driven so that it revolves is located between radially inner and outer lateral guides that border the track (6.1-6.4), and that (13.1-13.3) are located above one another on sectors of the outer lateral guide (9) one, each of which stationary transfer chutes receives the caps (10) from a top carrier ring (6.1) and delivers them in a downward and outward arrangement to the next-lower carrier ring (6.2), whereby a feed (11) feeds caps (10) to the topmost carrier ring (6.1) and a discharge (14) removes caps (10) from the lowest carrier ring (6.4).

One feature or aspect of an embodiment is believed at the time of the filing of this patent application to possibly reside broadly in a sterilizing device for caps for beverage containers, whereby the caps are guided along a trajectory in at least one track, with a closed housing through which gas flows and through which the trajectory runs, whereby the trajectory is arranged inside the housing so that it runs downward while encircling a vertical axis a plurality of times, characterized by the fact that for each revolution, a carrier ring that is driven so that it revolves is located between radially inner and outer lateral guides that border the track, and that are located above one another on sectors of the outer lateral guide one, each of which stationary transfer chutes receives the caps from a top carrier ring and delivers them in a downward and outward arrangement to the next-lower carrier ring, whereby a feed feeds caps to the topmost carrier ring and a discharge removes caps from the lowest carrier ring.

Another feature or aspect of an embodiment is believed at the time of the filing of this patent application to possibly reside broadly in a sterilizing device, characterized by the fact that the carrier rings and/or the lateral guides and/or the transfer chutes and/or the feed and/or the discharge are realized so that they are gas-permeable.

Yet another feature or aspect of an embodiment is believed at the time of the filing of this patent application to possibly reside broadly in a sterilizing device, characterized by the fact that the feed is realized so that its terminal piece matches the terminal piece of a transfer chute.

Still another feature or aspect of an embodiment is believed at the time of the filing of this patent application to possibly reside broadly in a sterilizing device, characterized by the fact that the discharge is realized so that its beginning piece matches the beginning piece of a transfer chute.

A further feature or aspect of an embodiment is believed at the time of the filing of this patent application to possibly reside broadly in a sterilizing device, characterized by the fact that the carrier rings are driven in synchronization with one another.

Another feature or aspect of an embodiment is believed at the time of the filing of this patent application to possibly reside broadly in a sterilizing device, characterized by the fact that the carrier rings are fastened to a drum that is driven in rotation and forms the inner lateral guide.

The components disclosed in the various publications, disclosed or incorporated by reference herein, may possibly be used in possible embodiments of the present invention, as well as equivalents thereof.

Some examples of bottling systems that may possibly be utilized or possibly adapted for use in at least one possible embodiment of the present application may possibly be found in the following U.S. patents, all assigned to the Assignee herein, namely: U.S. Pat. Nos. 4,911,285; 4,944,830; 4,950,350; 4,976,803; 4,981,547; 5,004,518; 5,017,261; 5,062,917; 5,062,918; 5,075,123; 5,078,826; 5,087,317; 5,110,402; 5,129,984; 5,167,755; 5,174,851; 5,185,053; 5,217,538; 5,227,005; 5,413,153; 5,558,138; 5,634,500; 5,713,403; 6,276,113; 6,213,169; 6,189,578; 6,192,946; 6,374,575; 6,365,054; 6,619,016; 6,474,368; 6,494,238; 6,470,922; and 6,463,964.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of stepping motors that may possibly be utilized or possibly adapted for use in at least one possible embodiment of the present application may possibly be found in the following U.S. patents: U.S. Pat. No. 6,348,774 issued to Andersen et al. on Feb. 19, 2002; U.S. Pat. No. 6,373,209 issued to Gerber et al. on Apr. 16, 2002; U.S. Pat. No. 6,424,061 issued to Fukuda et al. on Jul. 23, 2002; U.S. Pat. No. 6,509,663 issued to Aoun on Jan. 21, 2003; U.S. Pat. No. 6,548,923 to Ohnishi et al. on Apr. 15, 2003; and U.S. Pat. No. 6,661,193 issued to Tsai on Dec. 9, 2003.

The appended drawings in their entirety, including all dimensions, proportions and/or shapes in at least one embodiment of the invention, are accurate and are hereby included by reference into this specification.

Some examples of sensors that may possibly be utilized or possibly adapted for use in at least one possible embodiment of the present application may possibly be found in the following U.S. patents: U.S. Pat. No. 6,062,248 issued to Boelkins on May 16, 2000; U.S. Pat. No. 6,223,593 issued to Kubisiak et al. on May 1, 2001; U.S. Pat. No. 6,466,035 issued to Nyfors et al. on Oct. 15, 2002; U.S. Pat. No. 6,584,851 issued to Yamagishi et al. on Jul. 1, 2003; U.S. Pat. No. 6,631,638 issued to James et al. on Oct. 14, 2003; and U.S. Pat. No. 6,707,307 issued to McFarlane et al. on Mar. 16, 2004.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of servo-motors that may possibly be utilized or possibly adapted for use in at least one possible embodiment of the present application may possibly be found in the following U.S. patents: U.S. Pat. No. 4,050,434 issued to Zbikowski et al. on Sep. 27, 1977; U.S. Pat. No. 4,365,538 issued to Andoh on Dec. 28, 1982; U.S. Pat. No. 4,550,626 issued to Brouter on Nov. 5, 1985; U.S. Pat. No. 4,760,699 issued to Jacobsen et al. on Aug. 2, 1988; U.S. Pat. No. 5,076,568 issued to de Jong et al. on Dec. 31, 1991; and U.S. Pat. No. 6,025 issued to Yasui on Feb. 15, 2000.

All, or substantially all, of the components and methods of the various embodiments may be used with at least one embodiment or all of the embodiments, if more than one embodiment is described herein.

Some examples of bottling systems which may possibly be utilized or adapted for use in at least one possible embodiment may possibly be found in the following U.S. patents: U.S. Pat. No. 6,684,602, entitled "Compact bottling machine;" U.S. Pat. No. 6,470,922, entitled "Bottling plant for bottling carbonated beverages;" U.S. Pat. No. 6,390,150, entitled "Drive for bottling machine;" U.S. Pat. No. 6,374,575, entitled "Bottling plant and method of operating a bottling plant;" U.S. Pat. No. 6,192,946, entitled "Bottling system;" U.S. Pat. No. 6,185,910, entitled "Method and an apparatus for high-purity bottling of beverages;" U.S. Pat. No. 6,058,985, entitled "Bottling machine with a set-up table and a set-up table for a bottling machine and a set-up table for a bottle handling machine;" U.S. Pat. No. 5,996,322, entitled "In-line bottling plant;" U.S. Pat. No. 5,896,899, entitled "Method and an apparatus for sterile bottling of beverages;" U.S. Pat. No. 5,848,515, entitled "Continuous-cycle sterile bottling plant;" U.S. Pat. No. 5,634,500, entitled "Method for bottling a liquid in bottles or similar containers;" and U.S. Pat. No. 5,425,402, entitled "Bottling system with mass filling and capping arrays."

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of low friction coatings which may possibly be utilized or adapted for use in at least one possible embodiment may possibly be found in the following U.S. patents: U.S. Pat. No. 6,551,718, entitled "Low friction coating;" U.S. Pat. No. 6,284,322, entitled "Low-friction coating composition;" U.S. Pat. No. 6,084,034, entitled "Functional coating for reducing friction;" U.S. Pat. No. 5,763,011, "Functional coating for reducing friction;" U.S. Pat. No. 5,674,951, entitled "Abrasion-resistant and low friction coating compositions;" U.S. Pat. No. 5,482,637, entitled "Anti-friction coating composition containing solid lubricants;" and U.S. Pat. No. 4,849,264, entitled "Friction reducing coating for metal surfaces."

All of the patents, patent applications and publications recited herein, and in the Declaration attached hereto, are hereby incorporated by reference as if set forth in their entirety herein.

Some examples of starwheels which may possibly be utilized or adapted for use in at least one possible embodiment may possibly be found in the following U.S. patents: U.S. Pat. No. 5,613,593, entitled "Container handling starwheel;" U.S. Pat. No. 5,029,695, entitled "Improved starwheel;" U.S. Pat. No. 4,124,112, entitled "Odd-shaped container indexing starwheel;" and U.S. Pat. No. 4,084,686, entitled "Starwheel control in a system for conveying containers."

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

Some examples of bottle closing machines which may possibly be utilized or adapted for use in at least one possible embodiment may possibly be found in the following U.S. patents: U.S. Pat. No. 4,389,833, entitled "Bottle closing machine having bottle neck washing arrangement;" U.S. Pat. No. 4,205,502, entitled "Rotary bottle closing machine;" U.S. Pat. No. 6,484,477, entitled "Capping machine for capping and closing containers, and a method for closing containers;" U.S. Pat. No. 6,430,896, entitled "Capping machine;" U.S. Pat. No. 5,918,442, entitled "In-line capping machine;" U.S. Pat. No. 5,400,564, entitled "Capping machine;" and U.S. Pat. No. 5,669,209, entitled "In-line capping machine."

All of the patents, patent applications or patent publications, which were cited in the International Search Report dated Feb. 12, 2004, and/or cited elsewhere are hereby incorporated by reference as if set forth in their entirety herein as follows: U.S. Pat. No. 2,278,434; WO 9846486; JP 11342917; and U.S. Pat. No. 3,318,439.

It will be understood that the examples of patents, published patent applications, and other documents which are included in this application and which are referred to in paragraphs which state "Some examples of . . . which may possibly be used in at least one possible embodiment of the present application . . ." may possibly not be used or useable in any one or more embodiments of the application.

The sentence immediately above relates to patents, published patent applications and other documents either incorporated by reference or not incorporated by reference.

The corresponding foreign and international patent publication applications, namely, Federal Republic of Germany Patent Application No. 102 38 633.1, filed on Aug. 19, 2002, having inventor Roland Topf, and DE-OS 102 38 633.1 and DE-PS 102 38 633.1, and International Application No. PCT/EP2003/008862, filed on Aug. 9, 2003, having WIPO Publication No. WO2004/018298 and inventor Roland Topf, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A beverage bottle cap treatment device comprising:

a housing being configured and disposed to house components of said treatment device in a housing space;

a cylindrical drum comprising a circular top surface, a circular bottom surface, and a cylindrical outer wall surface disposed between said top and bottom surfaces;

said cylindrical drum having a central vertical rotational axis about which said cylindrical drum is configured to rotate;

a plurality of circular carrier rings each having a diameter and being configured and disposed to carry bottle caps thereon;

said plurality of carrier rings comprising at least a top carrier ring and a bottom carrier ring;

said carrier rings being mounted substantially concentrically on said cylindrical wall portion to permit rotation of said carrier rings about said central vertical rotational axis;

said cylindrical wall portion being configured and disposed to form an inner lateral guide structure to guide bottle caps on said carrier rings;

an outer lateral guide structure being disposed opposite said inner lateral guide structure and being configured to guide bottle caps on said carrier rings;

said carrier rings being disposed between said inner lateral guide structure and said outer lateral guide structure;

a plurality of stationary transfer chutes comprising side boundary walls to guide bottle caps therein;

each of said transfer chutes being configured and disposed to permit transfer of bottle caps from an upper carrier ring to a next-lower carrier ring of a corresponding pair of successive carrier rings, at least a portion of which lower carrier ring is disposed directly below the upper carrier ring;

each of said transfer chutes comprising a substantially flat upper portion, a substantially curved and downwardly angled intermediate portion, and a substantially flat lower portion;

each of said transfer chutes being configured and disposed to follow a path to project outwardly and downwardly from an upper carrier ring and downwardly and inwardly toward a lower carrier ring of a corresponding pair of successive carrier rings;

a feed chute being configured and disposed to run downwardly into said housing and toward said top carrier ring to feed caps onto said top carrier ring;

said feed chute comprising a substantially flat, vertically-oriented upper portion, a substantially curved and inwardly-angled intermediate portion, and a substantially flat lower portion disposed adjacent said top carrier ring;

a discharge chute being configured and disposed to run downwardly out of said housing and away from said bottom carrier ring to remove caps from said bottom carrier ring;

said discharge chute comprising a substantially flat, vertically-oriented lower portion, a substantially curved and outwardly-angled intermediate portion, and a substantially flat upper portion disposed adjacent said bottom carrier ring;

said housing comprising a treatment gas inlet being configured and disposed to permit flow of treatment gas into said housing space, and a treatment gas outlet being configured and disposed to permit flow of treatment gas out of said housing space; and at least one of: said housing, said carrier rings, said lateral guide structures, said transfer chutes, said feed chute, and said discharge chute being configured and disposed to guide the flow of treatment gas over bottle caps in said treatment device.

2. The treatment device according to claim 1, wherein at least one of: said carrier rings, said lateral guide structures, said transfer chutes, said feed chute, and said discharge chute is gas-permeable to permit flow of treatment gas therethrough.

3. The treatment device according to claim 2, wherein:
said outer lateral guide structure comprises a substantially C-shaped guide plate disposed to concentrically encircle a portion of each of said carrier rings; and
said transfer chutes are disposed at the ends of said guide plate and extend across the space between the ends of said guide plate.

4. The treatment device according to claim 3, wherein:
the shape of said lower portion of said feed chute substantially matches the shape of said lower portion of a transfer chute; and
the shape of said upper portion of said discharge chute substantially matches the shape of said upper portion of a transfer chute.

5. The treatment device according to claim 4 in combination with a beverage bottle capping machine configured and disposed to close tops of filled beverage bottles, wherein:
said treatment device is configured and disposed to convey bottle caps to said capping machine;
said capping machine comprises a rotor and a plurality of capping devices disposed on the periphery of said rotor; and
each of said capping devices is configured and disposed to receive a bottle cap from said treatment device and place the cap on a corresponding beverage bottle to close the beverage bottle.

6. The treatment device in combination with a capping machine according to claim 5, and further in combination with a beverage bottle filling machine configured and disposed to fill beverage bottles, wherein:
said filling machine comprises a rotor and a plurality of filling devices disposed on the periphery of said rotor;
each of said filling devices is configured and disposed to fill a bottle with a liquid beverage; and
at least one of: said filling machine and said capping machine comprises a conveyer arrangement configured and disposed to move filled bottles out of said filling devices and into said capping devices.

7. The treatment device according to claim 1, wherein:
at least one of: said carrier rings, said lateral guide structures, said transfer chutes, said feed chute, and said discharge chute is gas-permeable to permit flow of treatment gas therethrough;
the shape of said lower portion of said feed chute substantially matches the shape of said lower portion of a transfer chute;
said treatment gas inlet is configured and disposed to permit flow of hydrogen peroxide gas into said housing space, and said treatment gas outlet is configured and disposed to permit flow of hydrogen peroxide gas out of said housing space to permit sterilization of bottle caps in said treatment device; and
the shape of said upper portion of said discharge chute substantially matches the shape of said upper portion of a transfer chute.

8. A container cap treatment device comprising:
a housing being configured and disposed to house components of said treatment device in a housing space;
a plurality of carrier rings being configured and disposed to carry caps thereon;
said plurality of carrier rings comprising at least a top carrier ring and a bottom carrier ring;
a rotatable structure being configured and disposed to rotate said carrier rings about a center axis;
an inner lateral guide structure being configured and disposed to guide container caps on said carrier rings;
an outer lateral guide structure being disposed opposite said inner lateral guide structure and being configured and disposed to guide container caps on said carrier rings;
said carrier rings being disposed between said inner lateral guide structure and said outer lateral guide structure;
a plurality of transfer chutes comprising side boundary walls to guide container caps therein;
each of said transfer chutes being disposed at said outer lateral guide structure;
each of said transfer chutes being configured and disposed to permit transfer of container caps from an upper carrier ring to a next-lower carrier ring of a corresponding pair of successive carrier rings, at least a portion of which lower carrier ring is disposed directly below the upper carrier ring;

each of said transfer chutes being configured and disposed to follow a path to project outwardly and downwardly from an upper carrier ring and downwardly and inwardly toward a lower carrier ring of a corresponding pair of successive carrier rings;

a feed chute being configured and disposed to feed caps onto said top carrier ring;

a discharge chute being configured and disposed to remove caps from said bottom carrier ring; and said housing comprising a treatment gas inlet being configured and disposed to permit flow of treatment gas into said housing space, and a treatment gas outlet being configured and disposed to permit flow of treatment gas out of said housing space.

9. The treatment device according to claim 8, wherein at least one of: said carrier rings, said lateral guide structures, said transfer chutes, said feed chute, and said discharge chute is gas-permeable to permit flow of treatment gas therethrough.

10. The treatment device according to claim 8, wherein the shape of said lower portion of said feed chute substantially matches the shape of said lower portion of a transfer chute.

11. The treatment device according to claim 8, wherein the shape of said upper portion of said discharge chute substantially matches the shape of said upper portion of a transfer chute.

12. The treatment device according to claim 8, wherein each of said carrier rings is configured to rotate in synchronization with one another.

13. The treatment device according to claim 12, wherein:
said rotatable structure comprises a cylindrical drum;
each of said carrier rings is mounted on the outer surface of said cylindrical drum; and
said outer surface of said cylindrical drum forms inner lateral guide structure.

14. The treatment device according to claim 8, wherein:
at least one of: said housing, said carrier rings, said lateral guide structures, said transfer chutes, said feed chute, and said discharge chute is configured and disposed to guide the flow of treatment gas over container caps in said treatment device; and
said treatment gas inlet is configured and disposed to permit flow of hydrogen peroxide gas into said housing space, and said treatment gas outlet is configured and disposed to permit flow of hydrogen peroxide gas out of said housing space to sterilize container caps in said treatment device.

15. The treatment device according to claim 14, wherein:
said outer lateral guide structure comprises a substantially C-shaped guide plate disposed to concentrically encircle a portion of each of said carrier rings; and
said transfer chutes are disposed at the ends of said guide plate and extend across the space between the ends of said guide plate.

16. The treatment device according to claim 15, wherein:
said rotatable structure comprises a cylindrical drum;
each of said carrier rings is mounted on the outer surface of said cylindrical drum; and
said outer surface of said cylindrical drum forms inner lateral guide structure.

17. The treatment device according to claim 16, wherein each of said transfer chutes comprises a substantially flat upper portion, a substantially curved and downwardly angled intermediate portion, and a substantially flat lower portion.

18. The treatment device according to claim 17, wherein:
said feed chute is configured and disposed to run downwardly into said housing and toward said top carrier ring;
said feed chute comprises a substantially flat, vertically-oriented upper portion, a substantially curved and inwardly-angled intermediate portion, and a substantially flat lower portion disposed adjacent said top carrier ring;
said discharge chute is configured and disposed to run downwardly out of said housing and away from said bottom carrier ring; and
said discharge chute comprises a substantially flat, vertically-oriented lower portion, a substantially curved and outwardly-angled intermediate portion, and a substantially flat upper portion disposed adjacent said bottom carrier ring.

19. The treatment device according to claim 14 in combination with a container capping machine configured and disposed to close tops of filled containers, wherein:
said treatment device is configured and disposed to convey caps to said capping machine;
said capping machine comprises a rotor and a plurality of capping devices disposed on the periphery of said rotor; and
each of said capping devices is configured and disposed to receive a cap from said treatment device and place the cap on a corresponding container to close the container.

20. The treatment device in combination with a capping machine according to claim 19, and further in combination with a container filling machine configured and disposed to fill containers, wherein:
said filling machine comprises a rotor and a plurality of filling devices disposed on the periphery of said rotor;
each of said filling devices is configured and disposed to fill a container with a liquid beverage; and
at least one of: said filling machine and said capping machine comprises a conveyer arrangement configured and disposed to move filled containers out of said filling devices and into said capping devices.

* * * * *